United States Patent
Sendl-Lang et al.

(10) Patent No.: US 8,084,427 B2
(45) Date of Patent: Dec. 27, 2011

(54) SUBCUTANEOUS IMPLANTS CONTAINING A DEGRADATION-RESISTANT POLYLACTIDE POLYMER

(75) Inventors: Anna Sendl-Lang, Munich (DE); Kai-Thomas Kramer, Bad Tötz (DE); Gregor Schütz, Otterfing (DE)

(73) Assignee: Hexel AG, Holzkirchen (DE)

( * ) Notice: Subject to any disclaimer, the term of this patent is extended or adjusted under 35 U.S.C. 154(b) by 458 days.

(21) Appl. No.: 12/293,758

(22) PCT Filed: Mar. 20, 2007

(86) PCT No.: PCT/EP2007/002447
§ 371 (c)(1),
(2), (4) Date: Sep. 19, 2008

(87) PCT Pub. No.: WO2007/107328
PCT Pub. Date: Sep. 27, 2007

(65) Prior Publication Data
US 2010/0168035 A1    Jul. 1, 2010

(30) Foreign Application Priority Data
Mar. 21, 2006    (EP) .................................. 06005707

(51) Int. Cl.
*A61K 38/22*    (2006.01)
*A61K 9/00*    (2006.01)

(52) U.S. Cl. .... 514/9.7; 514/19.4; 514/19.5; 514/772.3; 424/426

(58) Field of Classification Search .................. None
See application file for complete search history.

(56) References Cited

U.S. PATENT DOCUMENTS
2005/0238618 A1 * 10/2005 Huang .................. 424/78.37

FOREIGN PATENT DOCUMENTS
| EP | 0058481 A1 | 8/1982 |
| WO | WO 93/24150 A1 | 12/1993 |
| WO | WO 98/09613 A1 | 3/1998 |
| WO | WO 03/022297 A1 | 3/2003 |

OTHER PUBLICATIONS

Nuutinen et al. ("Effect of gamma, ethylene oxide, electron beam, and plasma sterilization on the behaviour of SR-PLLA in vitro," J. Biomat. Sci. Polymer Edn. (2002) 13 1325-1326).*
Soriano et al. ("Biodegradable implantable fluconazole delivery rods designed for the treatment of fungal osteomyelitis: Influence of gamma sterilization," J. Biomed Materials Research Part A, (2006) 77 632-638).*
Horáček et al. ("Influence of Molecular Weight on the Resistance of Polylactide Fibers by Radiation Sterilization," J. Applied Polymer Sci (1993) 50 1-5).*
Edlund et al. ("Degradable Polymer Microspheres for Controlled Drug Delivery," Adv in Polymer Sci (2002) 157 67-112).*
PCT International Search Report—(PCT/EP2007/002447) Date of Mailing Jan. 30, 2008.
Nugroho et al., "Degradation of poly(L-lactic acid) by γ-irradiation", *Polymer Degradation and Stability*, 2001, vol. 72, pp. 337-343.
Abstract of CN 1200032A, published on Nov. 25, 1998 and the English abstract from the PCT counterpart.

* cited by examiner

*Primary Examiner* — Christina Bradley
(74) *Attorney, Agent, or Firm* — Foley & Lardner LLP; Michel Morency

(57) ABSTRACT

The present invention refers to compositions comprising a LH-RH-analogue and/or pharmaceutically acceptable salts thereof in a low-dose and a degradation-resistant polylactide suitable for the preparation of subcutaneous implants. Sterilization of the polylactide via gamma-radiation as well as temperature stress result in a negligible decomposition of less than 1000 Dalton.

21 Claims, 2 Drawing Sheets

SUBCUTANEOUS IMPLANTS CONTAINING A DEGRADATION-RESISTANT POLYLACTIDE POLYMER

RELATED APPLICATIONS

This application is a National Phase Entry of PCT/EP2007/002447 filed Mar. 20, 2007, which claims priority to European Application No. 06 005 707 filed Mar. 21, 2006, herein by reference in their entireties.

FIELD OF THE INVENTION

The present invention relates to compositions comprising a luteinizing hormone releasing hormone analogue (hereafter LH-RH analogue) in a low content and a degradation-resistant polylactide suitable for the preparation of subcutaneous implants. The polylactide is resistant to sterilisation and/or temperature stress. Sterilisation of the implant via gamma-radiation as well as temperature stress result in a negligible decomposition of the polylactide of less than 1000 Dalton.

LH-RH analogues are used to treat diseases like hormone-dependent tumors such as prostate and breast cancer.

Commercially available prolonged release formulations containing LH-RH analogues include microparticles, microcapsules or implants which, when injected subcutaneously or intramuscularly, release the LH-RH analogue from a biodegradable matrix. As biodegradable polymer, typically a poly(lactide-co-glycolide) co-polymer is used. Some of the commercial products (e.g. Zoladex®) additionally have to contain a desiccant to prevent polymer degradation.

Microcapsules or microparticles have the following disadvantages:
- microcapsules or microparticles show a high initial burst, due to their huge surface area
- microcapsules or microparticles tend to have a non-continuous release rate
- they are suitable for delivering the LH-RH analogue for up to 3 months, maximally. Microcapsules or microparticles are administered to the patients as a suspension in a liquid medium. For a longer treatment a large number of microcapsules have to be administered, combined with a larger volume for injection. Such a treatment is very painful for the patients. An alternative would be a high loading of the microcapsules or microparticles with the LH-RH-analogue. But this could result in a uncontrolled release profile of the LH-RH analogue.
- due to the manufacturing process microparticles contain residual organic solvents like e.g. methylenechloride.

Another type of prolonged release formulation are implants. They have the following advantages:
- an implant can be administered directly to the patient without the need of a suspension medium, thus reducing the volume of material to be injected
- an implant shows a continuous release profile
- an implant needs less active ingredient than a microcapsule or microparticle to achieve the same release rate
- production is less complicated. Organic solvents can be avoided during manufacture.

EP 058 481 describes monolithic implants comprising a biodegradable heterogeneous poly(lactide-co-glycolide) co-polymer and an LH-RH agonist.

EP 839 525 describes microcapsule comprising a polymer of lactic acid having a weight-average molecular weight of 25000 to 60000.

WO 98/47489 describes implants comprising a biodegradable polymer with a logarithmic viscosity number between 0.5 dl/g and 1.6 dl/g in $CHCl_3$. The implants release the active ingredient over a prolonged period up to three month or more.

WO 03/002092 describes a controlled release composition, e.g. microcapsules, comprising a lactic acid polymer having a weight-average molecular weight of 15000 to 50000 Dalton in which the content of polymers having molecular weights of 5000 Dalton or less is about 5% by weight or less.

WO 03/022297 describes monolithic implants comprising a polylactide polymer having a weight-average molecular weight of from 12000 to 40000 Dalton and from 25 to 40% by weight of LH-RH analogue based upon the total weight of the implant. These implants release the LH-RH analogue over a period of at least 6 months.

WO 98/09613 describes a process of manufacturing implants comprising a peptide and a copolymer of lactic acid and glycolic acid having a ratio of glycolide to lactide units from about 0 to 5:1. The copolymer is sterilized with a dose of 1 to 2.5 Mrads of ionising gamma-radiation.

WO 93/24150 describes extended release compositions comprising a salt of a peptide with a carboxy-terminated polyester, for example a polylactide.

Before administration to a patient the implants have to be sterilised. Heat-sterilisation is not possible, because most polymers have a glass-transition temperature below 100° C. Therefore sterilisation is achieved with gamma-radiation with an irradiation dose of usually more than 25 kGy. Such a dose results in the formation of radicals in the polymer. Thus, gamma-radiation results in the degradation of the polymer accompanied by a change of the release profile for the active ingredient.

Implants should be storable over a longer period of time. In general, polylactides tend to hydrolyse in the presence of humidity or water at increased temperatures. Frequently a desiccant has to be added to the implant to achieve a sufficient storage stability.

The objective of the present invention is to develop an implant that is resistant to gamma-radiation and/or degradation caused by temperature stress. The implant should contain the LH-RH analogue in a low dose. Nevertheless the implant should be able to release the LH-RH analogue continuously for a period of at least 3 months.

Surprisingly a composition was found comprising an LH-RH analogue and a polylactide being resistant to gamma-radiation and/or temperature stress. The polylactide polymer shows a degree of decomposition of less than 1000 Dalton relative to the weight-average molecular weight of the polymer after sterilisation via gamma-radiation of the implant. The implant shows a storage stability of more than 24 months at elevated temperatures (about 30° C.). No desiccant is required. Therefore the implant can be used in countries of climate zone 4 (definition according to ICH-regulations). These compositions are suitable for preparing subcutaneous implants which allow the low-dosed LH-RH-analogue to be released over a period of time of more than 3 months.

It has been found that the resistance of the polylactide to gamma-radiation and/or temperature stress is due to a low weight-average molecular weight of the polylactide, preferably 4800 to 8600 Dalton. This is due to the fact that radiation and/or temperature stress causes less fractions in a short polymer chain of a polylactide than in a long polymer chain. Therefore, a polylactide having a low weight-average molecular weight shows less decrease in the weight-average molecular weight after radiation and/or temperature stress, preferably less than 1000 Dalton. If the decrease of the average-weight molecular weight of the polylactide is less than 1000 Dalton, the release rate of the LH-RH analogue from the implant is more predictable after radiation and/or temperature stress. Thus a high quality of the implant and improved safety for the patient can be achieved.

Surprisingly it was found that an implant having a relatively low content of LH-RH analogue, in particularly an amount less than about 6 mg Leuprorelin, provided a sufficient high release rate to achieve a therapeutic testosterone suppression of at least 3 months.

SUMMARY OF THE INVENTION

The present invention relates to a monolithic implant comprising
(i) a luteinizing hormone releasing hormone analogue (=LH-RH analogue) or a pharmaceutically acceptable salt thereof in an amount of less than 25% per weight of the total composition and
(ii) a homogenous polylactide polymer, being resistant to degradation caused by gamma-radiation and/or temperature stress,
wherein the degradation-resistant polylactide polymer shows a degree of decomposition of less than 1000 Dalton relative to the weight-average molecular weight of the polymer after gamma-irradiation is performed with an irradiation dose of between about 25 and 40 kGy of ionising gamma-radiation and/or
wherein the degradation-resistant polylactide polymer shows a degree of decomposition of less than 1000 Dalton relative to the weight-average molecular weight of the polymer after temperature stress, at a temperature of about 30° C. over a period of at least 24 months.

DETAILED DESCRIPTION OF THE INVENTION

Figure 1:
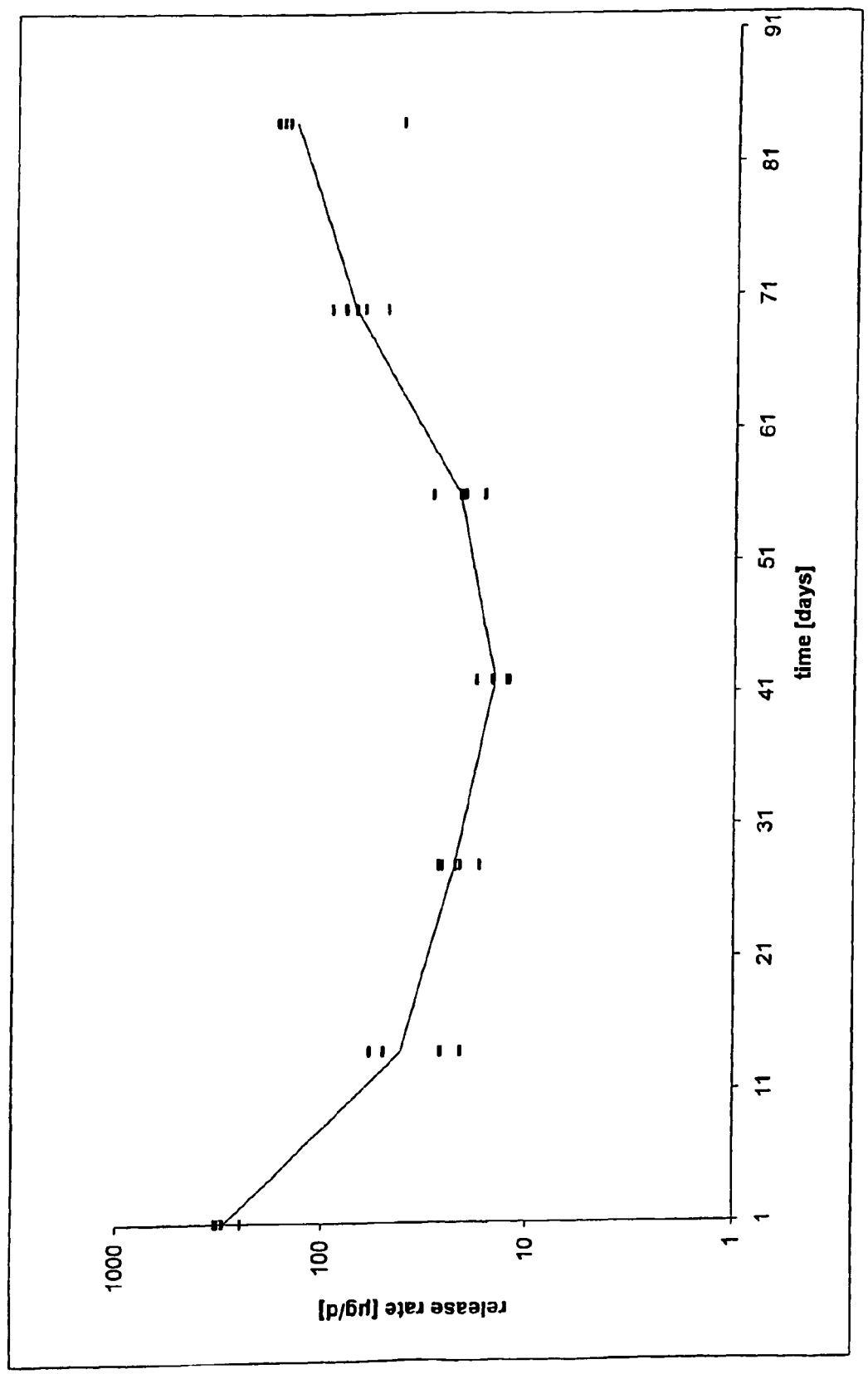
FIG. 1 shows an in-vitro release profile of Leuprorelin from a polylactide implant at 37° C. according to example 2.

The present invention relates to compositions comprising a low-dosed LH-RH-analogue and a degradation-resistant polylactide suitable for preparations of prolonged-release subcutaneous implants. The polylactide is resistant to degradation caused by gamma-radiation and/or temperature stress.
Polylactide Polymer The present invention relates to a monolithic implant wherein the degradation-resistant polylactide polymer shows a degree of decomposition of less than 1000 Dalton after gamma-radiation and/or temperature stress.

According to the present invention gamma-irradiation is performed with a dose of between about 25 and 40 kGy of ionising gamma-radiation.

According to the present invention temperature stress is a temperature of about 30° C. over a period of at least 24 months.

The present invention relates to a monolithic implant wherein the degradation-resistant polylactide polymer has a weight-average molecular weight of 4800 to 8600 Dalton, preferably of 5100 to 7800 Dalton and more preferably of 6700 to 7500 Dalton.

The present invention relates to a monolithic implant wherein the degradation-resistant polylactide polymer has a polydispersity index of 1.2 to 2.2, preferably 1.4 to 1.8.

The present invention relates to a monolithic implant wherein the degradation-resistant polylactide polymer has an inherent viscosity from 0.10 to 0.40 dl/g, preferably from 0.12 to 0.36 dl/g, especially from 0.16-0.24 dl/g.

The present invention relates to a monolithic implant wherein the degradation-resistant polylactide polymer has a acid number of more than 10 mg KOH per gram polylactide.

The present invention relates to a monolithic implant wherein the degradation-resistant polylactide polymer has a content of polymers having molecular weights of 2700 Dalton or less of more than 5% by weight, preferably more than 6% by weight and most preferably more than 8% by weight.

The degradation-resistant polylactide polymer is a homopolymer wherein all the repeat units of the polymer are of the formula (I)

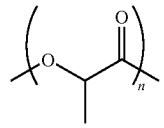

Formula I

The repeat units may be in the L-, D- or a mixture of the L- and D-configurations. Preferred is a Poly(D,L-lactide).

Gamma-radiation may result in the formation of radicals in a polymer. Thus the weight-average molecular weight of the polymer may decrease due to gamma-radiation.

In general polylactides tend to hydrolyse at increases temperatures in the presence of humidity, e.g. residual humidity during storage of the polylactide in a pouch. Thus the weight-average molecular weight of the polylactide may decrease due to temperature stress.

Degradation-resistant polylactide polymer within the meaning of the present patent is defined as a decrease of the weight-average molecular weight of the polymer of less than 1000 Dalton after the polymer has been exposed to gamma-radiation and/or temperature stress.

The degradation-resistant polylactide polymer shows a degree of decomposition of less than 1000 Dalton after sterilisation. Sterilisation is obtained with an irradiation dose of between about 25 and 40 kGy, preferably between about 26 and 35 kGy and more preferably between about 26 and 32 kGy of ionising gamma-radiation.

The degradation resistant polymer shows a degree of decomposition of less than 1000 Dalton after storage for more than 24 months at 30° C.

The weight-average molecular weight (Mw) of the degradation-resistant polylactide polymer is from 4800 to 8600 Dalton, preferably from 5100 to 7800 Dalton, more preferably from 6700 to 7500 Dalton. The weight-average molecular weight (Mw) of the polymer is measured using gel permeation chromatography (GPC) using polymer solutions in tetrahydrofurane (THF). Polylactide standards are used for calibration.

The present invention relates to a degradation-resistant polylactide polymer which is homogenous. By a "homogenous polylactide" it is meant a polylactide consisting solely of lactic acid monomers and showing a low polydispersity. "Low polydispersity" means a small variation in the molecular weight of the individual polylactide polymer chains.

The polydispersity index of the degradation-resistant homogenous polylactide polymer is from 1.2 to 2.2, preferably from 1.4 to 1.8. The polydispersity provides an indication of the spread/distribution of the chain lengths and is defined as the ratio (Mw)/(Mn) of the weight-average molecular weight (Mw) to the number-average molecular weight (Mn).

The degradation-resistant polylactide polymer has a content of polymers having molecular weights of 2700 Dalton or less of more than 5% by weight, preferably more than 6% by weight and most preferably more than 8% by weight.

The inherent viscosity of the degradation-resistant polylactide polymer is preferably from 0.10 to 0.40 dl/g, more preferably from 0.12 to 0.36 dl/g, most preferably from 0.16 to 0.24. The viscosity is measured in chloroform at a concentration of 0.1 g/dl (0.1%) at 25° C.

The hydrophilic character could be determined by the acid number. The acid number of the degradation-resistant polylactide polymer is preferably at least 10 mg KOH per gram polymer, preferably 10 to 12 mg KOH per gram polymer.

The degradation-resistant polylactide polymer may comprise a single polylactide homopolymer or a mixture of two or more polylactide homopolymers.

The degradation-resistant polylactide polymer may be prepared by the following methods. Suitable techniques may be a condensation polymerisation of lactic acid or a ring-opening polymerisation of lactide (cis-(±)-3,6-dimethyl-1,4-dioxane-2,5-dione). The ring-opening polymerisation is performed at elevated temperature and in the presence of a suitable catalyst. Suitable catalysts are for example zinc, antimony or organic tin-salts like tin-II-octoate. A suitable reaction temperature is from 120 to about 240° C., preferably from 170 to 190° C. The ring-opening polymerisation is performed over a period from 1 to 10 hours, preferably from 4 to 6 hours. The ring-opening polymerisation may be performed in the presence of a suitable chain termination agent thereby controlling the molecular weight of the resultant polylactide polymer. Suitable agents include water, lactic acid or an alcohol. Preferred is lactic acid as chain termination agent. Therefore, the preferred Poly(D,L-lactide) predominantly contains carboxylic end groups.

LH-RH Analogue

The present invention relates to a monolithic implant wherein the LH-RH analogue is selected from the group comprising Leuprorelin, Buserelin, Goserelin, Triptorelin, Nafarelin, Gonadorelin, Cetrorelix, Ganirelix or a pharmaceutically acceptable salt thereof.

The present invention relates to a monolithic implant wherein the LH-RH analogue is Leuprorelin.

The present invention relates to a monolithic implant wherein the LH-RH analogue is Goserelin.

The present invention relates to a monolithic implant wherein the amount of the LH-RH analogue is from 15 to 24%, more preferably from 18 to 23% by weight based upon the total weight of the implant.

The LH-RH-analogue may be an LH-RH agonist or a pharmaceutical acceptable salt thereof, or an LH-RH antagonist or a pharmaceutical acceptable salt thereof. Preferred LH-RH analogues are peptides or peptide derivatives.

Examples for suitable LH-RH agonists are Leuprorelin, Buserelin, Goserelin, Triptorelin, Nafarelin or Gonadorelin.

Examples for suitable LH-RH antagonists are Cetrorelix or Ganirelix.

Suitable salts of LH-RH analogues may be formed with inorganic acids (e.g. hydrochloric acid, hydrobromic acid, sulphuric acid, nitric acid, phosphoric acid) or organic acids (e.g. acetic acid, propionic acid, hydroxyacetic acid, lactic acid, pyruvic acid, oxalic acid, maleic acid, malonic acid, succinic acid, fumaric acid, malic acid, tartraic acid, citric acid, methanesulfonic acid, ethanesulfonic acid, benzenesulfonic acid, p-toluenesulphonic acid, cyclohexanesulphamic acid, salicylic acid, p-aminosalicylic acid and pamoic acid). The salts may be in an solvated form. Such solvates are e.g. hydrates or alcoholates.

An example for a suitable salt of a LH-RH agonist is Leuprorelin acetate.

Suitable salts of LH-RH analogues may be alkali metal and/or alkaline earth metal salts as well as ammonium salts such as, for example, the potassium, sodium, lithium, calcium-, magnesium- or ammonium salts.

According to the invention the implant may comprise mixtures of different LH-RH analogues, mixtures of different salts of a certain LH-RH analogue or mixtures of different salts of different LH-RH analogues.

According to the present invention the monolithic implant comprises less than 25%, preferably from 15 to 24%, more preferably from 18 to 23% by weight of the LH-RH analogue based on the total weight of the implant.

The preferred LH-RH-analogue is Leuprorelin or Goserelin in an amount of 22% by weight based on the total weight of the implant.

The LH-RH analogue or a pharmaceutically acceptable salt thereof, for example Leuprorelin acetate, is embedded in the polylactide matrix. Preferably the LH-RH analogue or a pharmaceutically acceptable salt thereof is homogenously embedded in the polylactide matrix. The LH-RH analogue does not form, and is not intended to form, a salt with the polylactide. For the purpose of the present invention a polylactide salt of LH-RH analogue is not intended to be a pharmaceutical acceptable salt of an LH-RH analogue.

Manufacture:

Implants according to the invention may be produced by a process comprising the steps of:
(i) dissolving the degradation-resistant polylactide polymer in an solvent,
(ii) mixing the polymer solution with an aqueous solution of the LH-RH analogue and/or pharmaceutically acceptable salts thereof,
(iii) removing substantially all of the solvent, and
(iv) extruding the product of step (ii) and dividing it into portions to form a monolithic implant of the required dimensions.

As solvent may be used water. The solvent may be removed for example by evaporation or freeze-drying.

The implants may also be produced by a process comprising the steps of:
(i) weighing the LH-RH-analogue and/or pharmaceutically acceptable salts thereof and the degradation-resistant polylactide polymer,
(ii) grinding the mixture below the glass transition temperature of the polylactide,
(iii) bringing the obtained homogenised mixture to room temperature, and
(iv) extruding the homogenised mixture and dividing it into portions to form monolithic implants of the required dimensions.

For grinding of the mixture a cryogenic mill may be used.

Extrusion may be carried out with a extrusion device at a temperature between 70 and 110° C. to form a continuous rod product. The cylindrical rods are cut into pieces of about 8 to 30 mm in length, preferably 9 to 11 mm.

Sterilisation

The monolithic implant has to be sterilised prior to administration to the patient. Sterilisation is, for example carried out with a dose of between about 25 and 40 kGy, preferably between about 26 and 35 kGy and more preferably between about 26 and 32 kGy of ionising gamma-radiation. Radiation of the implant with a dose above 25 kGy results in a sterile product, fulfilling the requirements regarding sterility demanded by authorities responsible for pharmaceutical approvals. Radiation within the above ranges causes a marginal decomposition of the LH-RH analogue, but the impurity content due to radiation induced decomposition in the implant is less than 1% of the overall amount of the analogue. This level of decomposition is accepted by the regulatory authorities.

Storage

The monolithic implant can be stored in the final container for a long period of time. The monolithic implant could be stored for at least 24 months up to a temperature of 30° C., preferably for 36 months up to a temperature of 30° C.

Implant

The implant of the present invention may be in form of cylinders, rods or spheres. Preferred are cylindrical rods. The cylindrical rods may have a diameter between 1 to 2 mm diameter, preferably between 1.4 and 1.7 mm and a length of between 8 to 30 mm, preferably 9 to 11 mm. The cylindrical rods are suitable for sub-dermal implantation into a patient, e.g., by using a needle for intramuscular or subcutaneous injection, or by sub-dermal surgical implantation. The implant has a LH-RH-analogue content of between 3 and 15 mg. The implant may contain Leuprorelin in a content of 4 to 6 mg, a diameter of 1.45 to 1.65 mm and a length of 9 to 11 mm. The implant may contain Goserelin in a content of 9 to 12 mg, a diameter of 1.45 to 1.65 mm and a length of 13 to 17 mm.

Release Profile

The present invention relates to a monolithic implant wherein the monolithic implant continuously releases the LH-RH analogue or a pharmaceutically acceptable salt thereof over a period of at least 3 month, preferably 3 to 4 months when placed in an aqueous physiological-type environment.

The monolithic implant continuously releases the LH-RH analogue over a period of at least 3 month, preferably over a period of 3 to 4 months when placed in an aqueous physiological-type medium.

After a short initial burst the LH-RH analogue is released continuously, preferably with a release rate of at least 4 μg/day. 80% of the LH-RH analogue by weight is released after a period of 3 month when the implant is placed in an aqueous physiological environment.

The mechanism of drug release from the monolithic implant after subcutaneous injection comprises an initial burst period, a lag period and an erosion period. The initial burst period of the monolithic implant results from the release of LH-RH analogue which is washed away from the surface of the implant by the surrounding medium. During the lag period the release rate of the drug is predominately defined by diffusion of dissolved drug through the pores of the matrix and the chemical degradation of the polylactide. As polylactide is a polyester, chemical degradation occurs by contact with water through the hydrolysis of the ester bondage's. Long polyester chains are hydrolysed to smaller chains with more hydrophilic character. When a high amount of soluble short-chain polymer degradation products (oligomeres and monomers) are formed, the erosion period begins. The monomers, oligomers and the drug are washed out of the implant. At the end of the erosion period the implant breaks down.

By the term "aqueous physiological environment" we mean the body, particular the musculature or the circulatory system, of a warm-blooded animal. As warm-blooded animal may be chosen dog, rabbit, rat or human. Human is preferred. For in-vivo measurement of the amount of released LH-RH analogue after the application of an implant to a warm-blooded animal, the concentration of the respective LH-RH analogue in serum samples is determined. The application of the monolithic implant to humans results in serum levels of the LH-RH analogue of at least 40 pg/ml over a period of at least 3 month, preferably 3 to 4 months. For Leuprorelin, the application of the monolithic implant to humans results in Leuprorelin mean serum levels of at least 40 pg/ml, preferably at least 50 pg/ml over a period of at least 3 month, preferably 3 to 4 months.

The release of the LH-RH analogue from the implant under in-vivo conditions may be simulated in vitro by placing an implant in an aqueous dissolution medium, optionally buffered to a physiological pH, at a temperature of 35 to 40° C. A suitable dissolution device comprises a high precision pump, flow through cell and a collecting device. Preferably the dissolution medium is maintained at a temperature of 37° C.

The present invention is further illustrated by the following examples, which are not to be construed as limitative.

Example 1

A mixture of polylactide and Leuprorelin acetate are weighted together, homogenised by grinding and subsequently transferred in the extrusion cylinder of a ram extruder. The mixture is then heated to about 70° C. to start the extrusion process. The molten mixture is then pressed by the force of a piston through the nozzle of the extruder and cooled to ambient temperature. The resulting continuous rope is stepwise cut to smaller pieces (implants) of about 1 cm length and inserted in an application device (syringe). The syringe is primary packed in an aluminium sachet, tightly sealed and sterilised by gamma sterilisation with a dose between 25 and 32 kGy.

The weight average molecular weight of polylactide is determined before and after sterilisation. The weight average molecular weight is measured by gel permeation chromatography (GPC). Measurements are conducted by high performance GPC apparatus according to the German guide line for industry DIN 55672. A combination of 3 columns is used having a pore size of 1000, 10000 and 100000 Angström, respectively. The column material is based on styroldivinylbenzole-copolymer (=SDV), having a particle size of 5 μm (Supplier: Polymer Standards Service PSS, Mainz, Germany). Polylactide standards (Supplier: Polymer Standards Service PSS, Mainz, Germany) with Mw of 144, 1600, 9750, 27800, 727, 2680, 19600, 43100 are used for calibration. Tetrahydrofurane is used as solvent for the polymer. The results in Table 1 show that the degradation of the polylactide is less than 1000 Dalton after sterilisation.

TABLE 1

| Batch | GPC before sterilisation | GPC after sterilisation | Gamma radiation dose | w/w % Leuprorelin by weight of implant | weight of implant |
| --- | --- | --- | --- | --- | --- |
| 1 | Mw = 4520 Dalton | Mw = 4300 Dalton | 28 kGy | 22.2% | 22.4 mg |
| 2 | Mw = 4840 Dalton | Mw = 4540 Dalton | 28 kGy | 22.2% | 22.6 mg |
| 3 | Mw = 7630 Dalton | Mw = 7460 Dalton | 25 kGy | 22.2% | 22.2 mg |

TABLE 1-continued

| Batch | GPC before sterilisation | GPC after sterilisation | Gamma radiation dose | w/w % Leuprorelin by weight of implant | weight of implant |
|---|---|---|---|---|---|
| 4 | Mw = 5680 Dalton | Mw = 5220 Dalton | 27 kGy | 22.2% | 22.9 mg |
| 5 | Mw = 5680 Dalton | Mw = 5610 Dalton | 13 kGy | 22.2% | 22.9 mg |
| 6 | Mw = 6700 Dalton | Mw = 6520 Dalton | 11.7-12.5 | 22.2% | 22.5 mg |
| 7 | Mw = 6700 Dalton | Mw = 6490 Dalton | 25.3-27.2 | 22.2% | 22.5 mg |
| 8 | Mw = 6700 Dalton | Mw = 6280 Dalton | 35.5-38.1 | 22.2% | 22.5 mg |

Example 2

In Vitro Release of Leuprorelin Implant

The dissolution characteristics of the implants are characterised by the following dissolution method. The principle of the described flow-through apparatus is according to the European Pharmacopoeia (Chapter 2.9.3., Dissolution test for solid oral dosage forms).

The implant is placed in the cylinder of a flow through cell which is closed at both ends with a sintered filterdisc. The medium (isotonic phosphate buffer (pH 7.4)) runs continuously through the chamber with the implant with a flow speed of approx. 0.3 ml/h. The whole cell is placed in a heated water bath at 37° C. One implant is assigned to one flow-through cell. The medium is collected at defined intervals and analysed by a suitable HPLC-method.

The in vitro release rates of Leuprorelin from the implant of batch 3 are shown in Table 2 and FIG. 1.

TABLE 2

In-vitro release of Leuprorelin from polylactide implant at 37° C.

| Day | Sample 1 Release of Leuprorelin in μg/d | Sample 2 Release of Leuprorelin in μg/d | Sample 4 Release of Leuprorelin in μg/d | Sample 5 Release of Leuprorelin in μg/d | Sample 6 Release of Leuprorelin in μg/d |
|---|---|---|---|---|---|
| 1 | 295.3 | 323.6 | 245.0 | 300.0 | 314.9 |
| 2 | 7.9 | 1.9 | 5.4 | 7.5 | 4.0 |
| 3 | 12.4 | 2.0 | 6.9 | 21.2 | 8.8 |
| 7 | 28.0 | 8.6 | 22.3 | 28.4 | 21.1 |
| 10 | 119.9 | 49.5 | 100.6 | 97.1 | 54.4 |
| 14 | 68.1 | 39.5 | 62.8 | 54.9 | 3.9 |
| 21 | 35.0 | 22.2 | 34.8 | 30.2 | 28.2 |
| 28 | 19.6 | 12.2 | 17.7 | 14.9 | 14.9 |
| 35 | 14.6 | 16.7 | 18.4 | 10.8 | 13.6 |
| 42 | 15.1 | 19.3 | 11.6 | 14.5 | 10.9 |
| 49 | 14.9 | 22.1 | 17.2 | 12.2 | 15.1 |
| 56 | 26.1 | 21.6 | 24.8 | 20.8 | 43.9 |
| 63 | 66.3 | 128.0 | 51.4 | 69.7 | 88.2 |
| 70 | 63.9 | 61.3 | 49.0 | 74.5 | 74.5 |
| 77 | 298.8 | 323.3 | 243.6 | 40.6 | 61.4 |
| 84 | 10.0 | 4.8 | 112.7 | 44.9 | 286.6 |
| 91 | 3.6 | 10.2 | 3.0 | 45.3 | 4.2 |
| 98 | 2.0 | 2.1 | 2.3 | 54.6 | 0.0 |

Example 3

In vivo Release of Leuprorelin Implant

An implant consisting of Leuprorelin acetate and polylactide is prepared according to example 1. The content calculated as Leuprorelin is 22.2 w/w % by weight of the implant. The weight average molecular weight of the polylactide is 7380 Dalton determined before sterilisation. The polydispersity index of the polylactide is 1.51.

An in vivo study of this Leuprorelin implant for pharmacokinetics is performed with the following parameters:

Number of patients: 15

Mode of administration: subcutaneous injection

Duration of treatment: 16 weeks (113 days)

Pharmacokinetics: Blood sampling for Leuprorelin on day 1, 2, 15, 29, 57, 85 and 113

Determination of Leuprorelin in human serum samples is carried out by the following method:

LC-MS/MS

Calibration range: 25-10000 pg/ml

Lowest limit of quantity: 25 pg/ml

Figure 2:
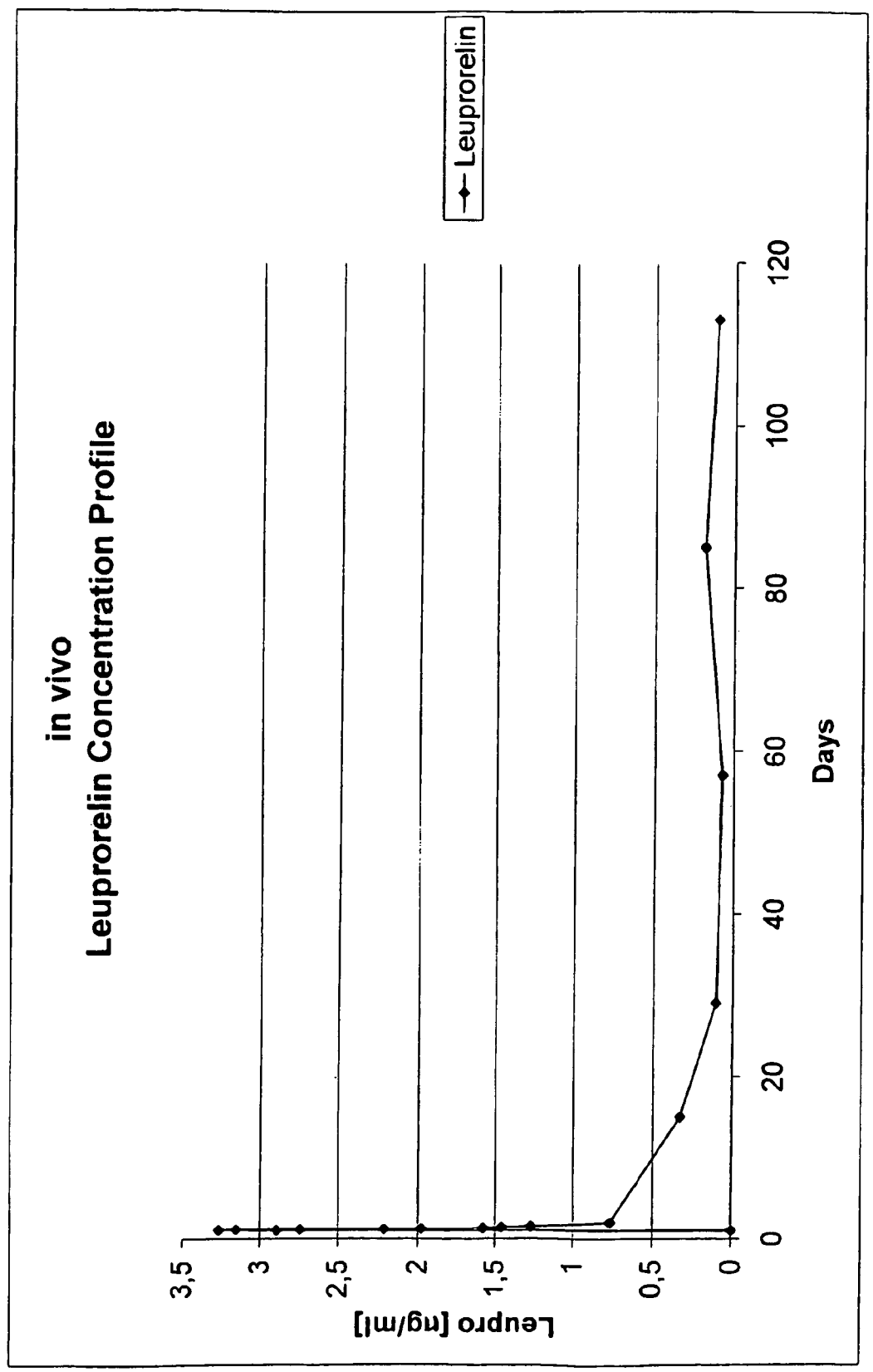
FIG. 2 shows an in-vivo release profile of Leuprorelin from a polylactide implant according to example 3

The in vivo release of Leuprorelin from the implant is shown in Table 3 and FIG. 2.

TABLE 3

In-vivo release of Leuprorelin from polylactide implant

| Day | Mean value of Leuprorelin in blood samples [ng/ml] | Number of patients |
|---|---|---|
| 1 | 0 | 15 |
| 1.042 | 2.892 | 15 |
| 1.083 | 3.265 | 15 |
| 1.125 | 3.153 | 15 |
| 1.167 | 2.74 | 15 |

TABLE 3-continued

In-vivo release of Leuprorelin from polylactide implant

| Day | Mean value of Leuprorelin in blood samples [ng/ml] | Number of patients |
| --- | --- | --- |
| 1.208 | 2.214 | 15 |
| 1.25 | 1.977 | 15 |
| 1.333 | 1.579 | 15 |
| 1.417 | 1.458 | 15 |
| 1.5 | 1.271 | 15 |
| 2 | 0.765 | 15 |
| 15 | 0.326 | 15 |
| 29 | 0.105 | 15 |
| 57 | 0.073 | 15 |
| 85 | 0.186 | 15 |
| 113 | 0.111 | 14 |

The invention claimed is:

1. A monolithic implant comprising:
(i) a luteinizing hormone releasing hormone analogue or a pharmaceutically acceptable salt thereof in an amount of less than 25% per weight of the total composition; and
(ii) a polylactide polymer that is resistant to degradation caused by gamma-radiation and/or temperature stress, wherein the degradation-resistant polylactide polymer is a homopolymer, wherein
all the repeat units of the polymer are of the formula (I);

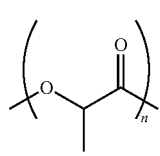

formula (I)

wherein the repeat units may be in the L-, D- or a mixture of the L- and D-configurations;
wherein the degradation-resistant polylactide polymer has a weight-average molecular weight of 4800 to 8600 Dalton; and
wherein the degradation-resistant polylactide polymer shows a degree of decomposition of less than 1000 Dalton relative to the weight-average molecular weight of the polymer after gamma-irradiation is performed with an irradiation dose of between about 25 and 40 kGy of ionizing gamma-radiation and/or wherein the degradation-resistant polylactide polymer shows a degree of decomposition of less than 1000 Dalton relative to the weight-average molecular weight of the polymer after temperature stress, at a temperature of about 30° C. over a period of at least 24 months.

2. The monolithic implant of claim 1, wherein the luteinizing hormone releasing hormone analogue is selected from the group consisting of: Leuprorelin, Buserelin, Goserelin, Triptorelin, Nafarelin, Gonadorelin, Cetrorelix, Ganirelix and pharmaceutically acceptable salts thereof.

3. The monolithic implant of claim 2, wherein the luteinizing hormone releasing hormone analogue is Leuprorelin.

4. The monolithic implant of claim 2, wherein the luteinizing hormone releasing hormone analogue is Goserelin.

5. The monolithic implant of claim 1, wherein the amount of the luteinizing hormone releasing hormone analogue is from 15 to 24% by weight based upon the total weight of the implant.

6. The monolithic implant of claim 1, wherein the degradation-resistant polylactide polymer has a weight-average molecular weight of 5100 to 7800 Dalton.

7. The monolithic implant of claim 1, wherein the degradation-resistant polylactide polymer has polydispersity index of about 1.2 to 2.

8. The monolithic implant of claim 1, wherein the degradation-resistant polylactide polymer has an inherent viscosity, measured in chloroform at a concentration of 0.1 g/dl at 25° C., between about 0.10 to 0.40 dl/g.

9. The monolithic implant of claim 1, wherein the degradation-resistant polylactide polymer has an acid number of more than 10 mg KOH per gram polylactide.

10. The monolithic implant of claim 1, wherein the degradation-resistant polylactide polymer is comprised of at least 5% by weight of polymers having molecular weights of 2700 Dalton or less.

11. The monolithic implant of claim 1, wherein the monolithic implant continuously releases the luteinizing hormone releasing hormone analogue or a pharmaceutically acceptable salt thereof over a period of at least three months when placed in an aqueous physiological-type environment.

12. The monolithic implant of claim 7, wherein the degradation resistant polylactide polymer has polydispersity index of about 1.4 to 1.8.

13. The monolithic implant of claim 8, wherein the degradation resistant polylactide polymer has an inherent viscosity between about 0.12 to 0.36 dl/g.

14. The monolithic implant of claim 8, wherein the degradation resistant polylactide polymer has an inherent viscosity between about 0.16 to 0.24 dl/g.

15. The monolithic implant of claim 10, wherein the degradation-resistant polylactide polymer is comprised of at least 6% by weight of polymers having molecular weights of 2700 Dalton or less.

16. The monolithic implant of claim 15, wherein the degradation-resistant polylactide polymer is comprised of at least 8% by weight of polymers having molecular weights of 2700 Dalton or less.

17. The monolithic implant of claim 11, wherein the monolithic implant continuously releases the luteinizing hormone releasing hormone analogue or a pharmaceutically acceptable salt thereof over a period of at least three four months when placed in an aqueous physiological-type environment.

18. The monolithic implant of claim 11, wherein the physiological-type environment is that of a mammal.

19. The monolithic implant of claim 18, wherein the mammal is a human.

20. The monolithic implant of claim 1, wherein the amount of the luteinizing hormone releasing hormone analogue is from 18 to 23% by weight based upon the total weight of the implant.

21. The monolithic implant of claim 1, wherein the degradation-resistant polylactide polymer has a weight-average molecular weight of 6700 to 7500 Dalton.

* * * * *

UNITED STATES PATENT AND TRADEMARK OFFICE
CERTIFICATE OF CORRECTION

PATENT NO. : 8,084,427 B2
APPLICATION NO. : 12/293758
DATED : December 27, 2011
INVENTOR(S) : Anna Sendl-Lang, Kai-Thomas Kramer and Gregor Schütz Page 1 of 1

It is certified that error appears in the above-identified patent and that said Letters Patent is hereby corrected as shown below:

On the cover page of the patent, item (73), please replace the Assignee information with the following corrected version:

-- (73) Assignee: Hexal AG ~~Hexel AG~~, Holzkirchen (DE) --

Signed and Sealed this
Twentieth Day of March, 2012

David J. Kappos
*Director of the United States Patent and Trademark Office*